(12) United States Patent
Engström et al.

(10) Patent No.: US 8,057,229 B2
(45) Date of Patent: Nov. 15, 2011

(54) DENTAL IMPLANT, ABUTMENT STRUCTURE AND METHOD FOR IMPLANTING A DENTAL IMPLANT

(75) Inventors: Kent Engström, Mölndal (SE); Anders Halldin, Uddevalla (SE)

(73) Assignee: Astra Tech AB, Molndal (SE)

( * ) Notice: Subject to any disclaimer, the term of this patent is extended or adjusted under 35 U.S.C. 154(b) by 381 days.

(21) Appl. No.: 12/073,217

(22) Filed: Mar. 3, 2008

(65) Prior Publication Data

US 2009/0291412 A1    Nov. 26, 2009

(30) Foreign Application Priority Data

Mar. 6, 2007    (EP) .................................... 07103620

(51) Int. Cl.
*A61C 8/00*    (2006.01)
(52) U.S. Cl. ........................................................ 433/173
(58) Field of Classification Search ................... 433/173, 433/174
See application file for complete search history.

(56) References Cited

U.S. PATENT DOCUMENTS

| | | | | |
|---|---|---|---|---|
| 5,035,619 A | * | 7/1991 | Daftary | 433/173 |
| 5,104,318 A | * | 4/1992 | Piche et al. | 433/174 |
| 5,120,221 A | | 6/1992 | Orenstein et al. | |
| 5,152,687 A | * | 10/1992 | Amino | 433/173 |
| 5,286,195 A | | 2/1994 | Clostermann | |
| 5,328,271 A | | 7/1994 | Titcomb | |
| 5,328,371 A | | 7/1994 | Hund et al. | |
| 5,344,457 A | * | 9/1994 | Pilliar et al. | 606/60 |
| 5,527,182 A | * | 6/1996 | Willoughby | 433/172 |
| 5,678,995 A | | 10/1997 | Kirsch et al. | |
| 5,810,592 A | | 9/1998 | Daftary | |
| 5,829,977 A | | 11/1998 | Rogers et al. | |
| 5,873,722 A | | 2/1999 | Lazzara et al. | |
| 6,290,499 B1 | | 9/2001 | Lazzara et al. | |
| 2002/0076673 A1 | | 6/2002 | Wagner et al. | |
| 2004/0076924 A1 | | 4/2004 | Kim | |

FOREIGN PATENT DOCUMENTS

| | | |
|---|---|---|
| EP | 0 687 450 | 12/1995 |
| EP | 0 630 621 | 12/1999 |
| JP | 7-275267 | 10/1995 |
| KR | 10-2004-0034867 | 4/2004 |
| KR | 10-2005-0082809 | 8/2005 |

OTHER PUBLICATIONS

XiVE Manual., "The System." Friadent. Article first located Apr. 26, 2006.
European Search Report dated Aug. 31, 2011 for Application EP 11157004.0-1318/2368519.

* cited by examiner

*Primary Examiner* — Ralph Lewis
(74) *Attorney, Agent, or Firm* — Harness, Dickey & Pierce, P.L.C.

(57) ABSTRACT

At least one embodiment of the present invention relates to a dental implant for supporting a coronal component. In at least one embodiment, the implant includes a fixture part forming an apical bone contact part of the implant, an abutment part forming a coronal component support part of the implant, and an abutment screw, wherein said abutment part is arranged to, in an assembled state of said dental implant, be fixed to the fixture part by the abutment screw, and wherein a coronal end portion of the abutment screw is arranged to, in the assembled state, be positioned coronally of a coronal end portion of the abutment part. At least one embodiment of the present invention also relates to abutment structures and methods for implanting a dental implant.

53 Claims, 1 Drawing Sheet

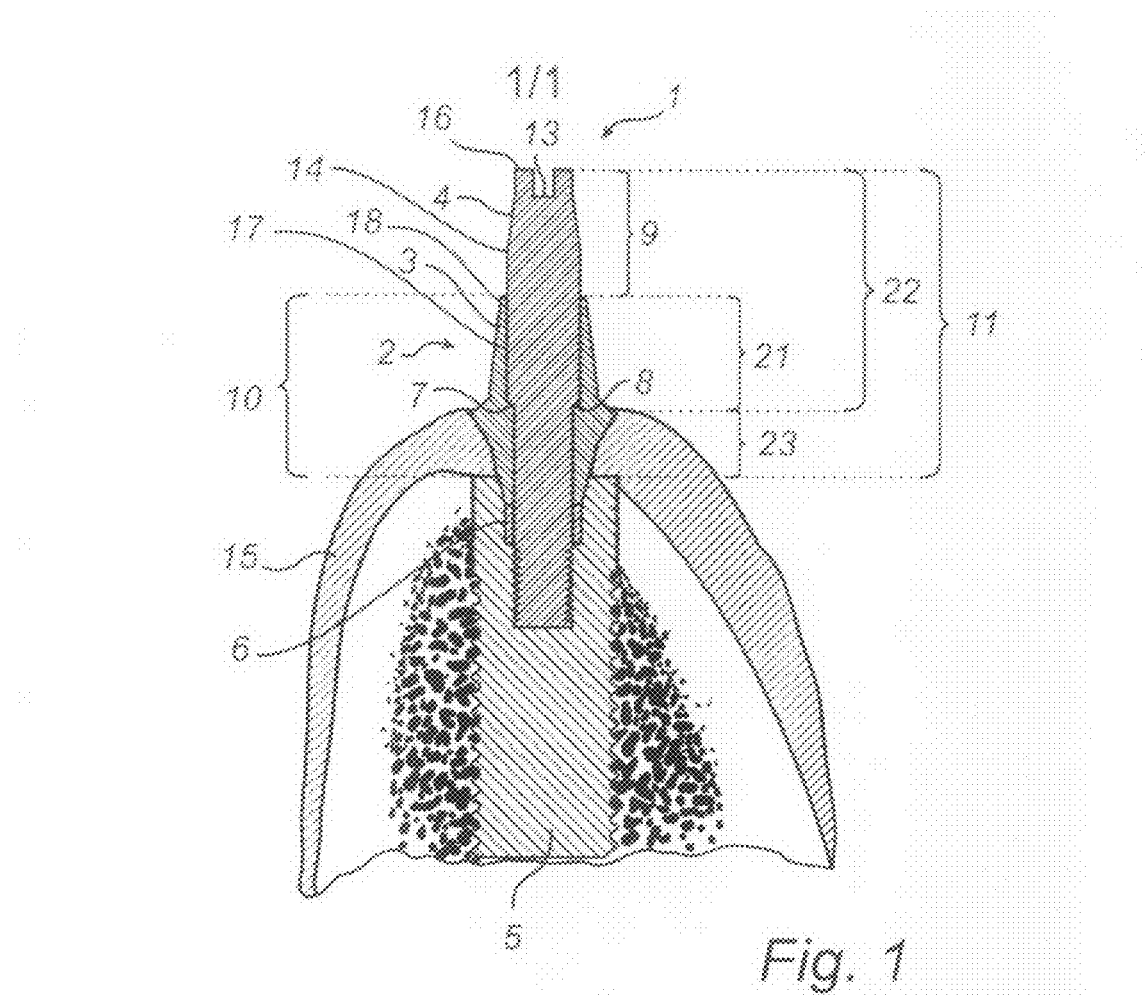
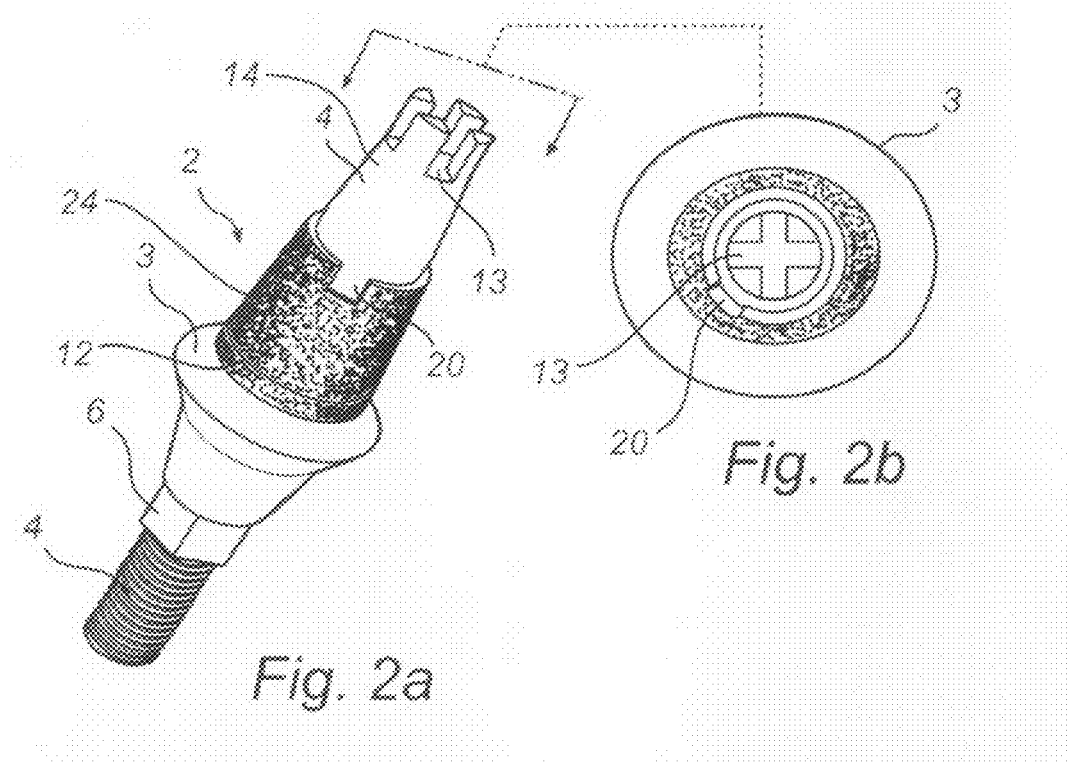

DENTAL IMPLANT, ABUTMENT STRUCTURE AND METHOD FOR IMPLANTING A DENTAL IMPLANT

TECHNICAL FIELD OF THE INVENTION

The present invention relates to a dental implant for supporting a coronal component, said implant comprising a fixture part forming an apical bone contact part of said implant, an abutment part forming a coronal component support part of said implant, and an abutment screw, wherein said abutment part is arranged to, in an assembled state of said dental implant, be fixed to said fixture part by said abutment screw.

The present invention also relates to an abutment structure for use in a dental implant adapted to support a coronal component, wherein said abutment structure is adapted to be supported by a fixture part of said implant, said abutment structure comprises at least an abutment part and an abutment screw, wherein said abutment part is adapted to be fixed to said fixture part by said abutment screw.

The present invention also relates to a method for implanting a dental implant.

BACKGROUND ART

Dental implant systems are widely used for replacing damaged or lost natural teeth. In such systems, a fixture part is usually implanted into the bone tissue of the maxilla or mandible of a patient in order to replace the natural tooth root. An abutment structure comprising one or several parts may then be attached to the fixture in order to build up a core for the part of the prosthetic tooth protruding from the bone tissue, through the soft gingival tissue and into the mouth of the patient. On said abutment structure, the prosthesis or crown may finally be seated.

As mentioned above, there exist dental implants where the abutment structure comprises one part and there exist dental implants where the abutment structure comprises two or more parts. When the abutment structure comprises several parts, a first part may be an abutment part that is arranged in relation to the fixture. For example, a portion of said abutment part might be partially inserted into a bore of said fixture. The portion of such an abutment part that is inserted into the fixture may for example comprise a hexagonal or a torx profile. The fixture then preferably comprises a corresponding profile, wherein the abutment part may become rotationally locked in relation to the fixture once the portion of the abutment comprising the profile is inserted into the fixture. The abutment part may also be a sleeve, which is arranged in relation to the fixture without any portion being inserted into the fixture. In either of these arrangements, a second part of the abutment structure may then be used to retain or hold the abutment part and the fixture in engagement. This holding element may for example be a screw. When the implant is in an assembled state, the screw may extend in a bore provided in the abutment part and the fixture along the substantially longitudinal extension of the abutment part and the fixture. In this case, the bore extending in the fixture preferably comprises a threaded portion for engagement with the threading of the screw.

The final prosthesis must be sized and configured so as to naturally fit with the remaining teeth of the patient, both for functionality and aesthetics. In order to size and configure the final prosthesis in accordance with the remaining teeth of the patient, the abutment structure has to be sized accordingly. Furthermore, since the abutment structure should be able to support a tooth-like prosthesis in an intended manner, it is advantageous if the abutment structure has an elongate shape, i.e. have a rather small diameter in relation to its height, such as natural teeth. The wall thickness of the abutment part may then become very small. This may relate especially to a two-part abutment structure, since it then is desirable to arrange a bore for the holding element in the abutment part. With concern taken to the desired height of the abutment structure, this may be difficult and costly to achieve from a production point of view.

Furthermore, the dental implant and the abutment structure of the dental implant may be subject to forces, that they must have the strength to withstand. These forces may occur both during the implantation of the dental implant into the patient's mouth and also during use, such as when a patient with a dental implant chews. If the wall thickness of the abutment structure supporting the prosthesis is to small in relation to the height of the structure, the strength of the abutment structure may become lower than desired and/or required.

Hence, there exists a need for a dental implant comprising an abutment structure with at least two parts that may be dimensioned accordingly for supporting prosthesis in a patient's mouth, without the above-mentioned problems regarding the strength of the abutment structure.

Therefore, it is an object of the present invention to provide a dental implant an abutment structure that meets this need.

SUMMARY OF THE INVENTION

The object of the present invention is met with a dental implant according to any one of the independent claims 1, 2 or 3. The object of the present invention is also met with an abutment structure according to any one of the independent claims 26, 27, 28. The object of the present invention is also met with a method according to any one of claims 50, 51, 52.

The term "coronal" is here and throughout this application used to indicate a direction towards a head end or trailing end of the component discussed. For example, in a situation where an abutment is connected to a fixture, the coronal direction of the abutment would be a direction towards the part of the abutment being directed away from the fixture. Likewise, the term "apical" indicates a direction towards an insertion end of the component. For an abutment connected to a fixture, the apical direction would be a direction towards the fixture. Thus, apical and coronal are opposite directions. Furthermore, the term "axial direction" is used throughout this application to indicate a direction taken from the coronal end to the apical end, or vice versa.

According to one aspect of the present invention a dental implant for supporting a cement-retained coronal component is provided, said implant comprising a fixture part forming an apical bone contact part of said implant, an abutment part forming a coronal component support part of said implant, and an abutment screw, wherein said abutment part is arranged to, in an assembled state of said dental implant, be fixed to said fixture part by said abutment screw, and wherein a coronal end portion of said abutment screw is arranged to, in said assembled state, be positioned coronally of a coronal end portion of said abutment part.

According to another aspect of the present invention a dental implant is provided, said dental implant comprising a fixture part forming an apical bone contact part of said implant, an abutment part forming a coronal component support part of said implant, and an abutment screw comprising a generally cylindrical coronal portion, wherein said abutment part is arranged to, in an assembled state of said dental implant, be fixed to said fixture part by said abutment screw, and wherein a coronal end portion of said abutment screw is arranged to, in said assembled state, be positioned coronally of a coronal end portion of said abutment part.

According to another aspect of the present invention a dental implant is provided, said dental implant comprising a fixture part forming an apical bone contact part of said implant, an abutment part forming a coronal component support part of said implant, and an abutment screw, wherein said abutment part is arranged to, in an assembled state of said dental implant, be fixed to said fixture part by said abutment screw, wherein said abutment screw comprises drive means arranged at a coronal end surface of said abutment screw, wherein said outer coronal end surface is substantially perpendicular to an axial direction of said abutment screw, and wherein a coronal end portion of said abutment screw is arranged to, in said assembled state, be positioned coronally of a coronal end portion of said abutment part.

A general idea of the invention is thus to provide a dental implant in which, when the implant is assembled, a portion of the abutment screw extends coronally of the coronal end portion of the abutment part. A coronal component such as a dental crown, a part of a dental bridge, a burn-out cylinder, a healing cap, a waxing sleeve or an impression pick-up will therefore, when mounted to said dental implant, be in contact with and become at least partially supported by the coronal portion of the abutment screw. It may be preferred that the coronal component also is in contact with and at least partly supported by the abutment part as well. For example, the abutment screw may support the coronal component in such a manner that it carries the force components that may act upon the coronal component in a direction perpendicular to the longitudinal axis of the dental implant. The abutment part may then support the coronal component in such a manner that it carries the rotational forces the coronal component may be subject to.

An abutment screw may be made as a solid piece. As a consequence of this, the above-mentioned problems with thin wall thickness of the part supporting the coronal component may be at least partly reduced. The strength of the abutment screw may therefore be satisfactorily high even when the diameter of the abutment screw is rather small in comparison to its height. Hence, the strength of the abutment structure may be satisfactorily high for both implantation and for supporting a coronal component.

It may be suitable that said abutment screw comprises drive means arranged at a coronal end surface of said abutment screw, and wherein said coronal end surface is substantially perpendicular to an axial direction of said abutment screw.

This may be a beneficial manner in how to arrange the drive means for tightening and releasing the abutment screw from the fixture part. The coronal end surface is then preferably the outer coronal end surface of the abutment screw. It is however also possible to arrange the drive means as, for example, an internal or external hexagonal profile at the coronal portion of the abutment screw. It may further be suitable that an apical portion of the abutment screw is provided with threads, in order to threadingly engage a corresponding portion of the fixture part when the dental implant is assembled.

Preferably, said dental implant is adapted to support a cement-retained coronal component.

A coronal component may be cement-retained to said dental implant. However, it may also be possible to arrange the abutment screw and/or the abutment part with threads in order to provide for screw-retaining a dental component to the dental implant.

Preferably, said abutment screw comprises a substantially cylindrical coronal portion.

The coronal portion may however also be provided with an external hexagonal profile or any other suitable profile.

Preferably, said drive means of said abutment screw comprises at least one notch.

At least one notch at the drive means may be a beneficial arrangement for enabling the tightening or removal of the abutment screw from the dental implant. It may also be suitable to provide the drive means with two notches. The notches may be arranged at the coronal end surface of the abutment screw and they may be perpendicular in relation to each other and intersecting each other. This arrangement may even further assist a user in tightening and removing of the abutment screw to and from the fixture of the dental implant.

Preferably said coronal end portion of said abutment screw forms a coronal end portion of said dental implant.

Preferably, said coronal end portion of said abutment screw extending coronally of said abutment part is arranged for supporting said coronal component.

By this, the coronal component may be at least partly supported by the coronal portion of the abutment screw. However, it may be preferred that the coronal component, when assembled to the dental implant, also is in contact with and is partly supported by the abutment part. For example, the abutment screw may support the coronal component in such a manner that it carries the force components that may act upon the coronal component in a direction perpendicular to the longitudinal axis of the dental implant and the rotational forces acting upon the coronal component may be carried by the abutment part. This provides for the possibility to arrange the dental implant to carry the necessary loads and at the same time design the dental implant with a desired shape, e.g. a design where the diameter of the dental implant is rather small in relation to its height.

Preferably, at least a portion of said abutment part has a conical shape tapered at least in a coronal direction of said dental implant.

Preferably, at least a portion of said abutment screw has a conical shape tapered at least in a coronal direction of said dental implant.

A tapering or angulated shape of the abutment part and/or the abutment screw assists in the positioning of the dental implant in a patient's jawbone. The shape of the jawbone where the dental implant is to be positioned may vary between different patients. Therefore, the borehole in the jawbone in which the fixture part is to be positioned sometimes has to be made in an inclined direction. When positioning several dental implants beside each other, a conflict may then arise when attempting to assemble a coronal component to a dental implant. This conflict may also arise with existing teeth surrounding the dental implant when only one dental implant is to be implanted. With a tapering or angulated shape of the abutment part and/or the abutment screw this conflict may be at least partly reduced. Hence, the tapered shape of either or both of the abutment part and the abutment screw increases the tolerance for drilling the holes in the patient's jawbone. It may be preferred that the abutment screw tapers at least in the portion that in an assembled state of said dental implant is adapted to extend coronally of the abutment part.

Preferably, said abutment part is provided with an internal bore extending in the axial direction of said abutment part, wherein said bore is provided with a tapering portion, which portion tapers in the apical direction of said abutment part.

An internal bore in said abutment part is beneficial for the insertion of the abutment screw through the abutment part. It is further advantageous if the internal bore of said abutment part is provided with a tapered portion, and the abutment screw is provided with a corresponding portion that is adapted to abut the tapered portion of the abutment part. This tapered portion, or shoulder, may then prevent axial movement of the abutment part in the assembled state of said dental implant, i.e. when the abutment screw extends through the bore and is arranged in threaded engagement with the fixture part.

Preferably, said abutment screw is arranged to, in said assembled state of said dental implant, extend in a bore arranged in said abutment and said fixture, respectively.

This is a beneficial manner in how to arrange the dental implant so that it may be assembled in the intended manner.

It may be preferred that said abutment part and/or said abutment screw is provided with a snap fitting arranged for engagement with said coronal component.

A snap fitting arranged at the abutment part and or the abutment screw may be a beneficial manner in how to secure a coronal component to the dental implant. The snap fitting may for example comprise a groove at the abutment part. The coronal component may then be provided with a corresponding portion that upon mounting of the coronal component to the dental implant may snap into the groove.

It may be preferred that at least a part of said abutment part, which is intended for supporting said coronal component, is provided with means for increasing the retention capability of said abutment part.

An increased retention capability, or frictional capability, may be advantageous in order to prevent the coronal component from being unintentionally separated from the dental implant. This increased retention capability may for example be provided by providing the abutment part with e.g. a blasted, etched, knurled or grooved surface.

Preferably, said abutment part is provided with one or more rotational stops for preventing an attached coronal component from rotation.

Once a coronal component is attached to the dental implant in a desired orientation, it is advantageous to limit the rotational possibility of the coronal component. The rotational stop may be arranged as a recess or cutout in the upper or coronal portion of the abutment part. A protrusion provided on the inner side of the coronal component may then be fitted into the recess, in the assembled state, in order to prevent or limit the rotational possibilities of the coronal component in relation to the dental implant. It is also possible to arrange several cut-outs or recesses, intended to function as rotational stops, at the coronal portion of the abutment part.

Preferably, at least a portion of an outer circumference of said abutment part, which is intended for supporting said coronal component, has a non-circular outline.

A non-circular outline of at least a portion of the abutment part is a beneficial manner in preventing or at least restraining the rotational possibilities of the coronal component in relation to the dental implant. The non-circular outline may for example be oval, squared, rectangular or triangular. Preferably, a portion of the inner surface of the coronal component, i.e. the portion that is in contact with the abutment part when the coronal component is mounted on the dental implant, has a corresponding shape.

Preferably, said coronal end portion of said abutment screw, that in said assembled state of said dental implant is extending coronally of a coronal end portion of said abutment part, has a length of 1-7 mm in the axial direction.

Preferably, the portion of said abutment part that during use may be in contact with a coronal component attached to said dental implant has a length of 1-5 mm in the axial direction.

Preferably, the portion of said abutment part that during use may be in contact with a coronal component attached to said dental implant has a length of 2-2.5 mm in the axial direction.

Preferably, the total length of the portion of the abutment part and the portion of the abutment screw that during use may be in contact with and support a coronal component is 3-8 mm in the axial direction.

The portions of an abutment structure of a dental implant, which in an assembled state is positioned coronally of the fixture part of the dental implant, may be considered as three portions. A first portion is the abutment part tissue extending portion. That is the portion of the abutment part that during use is positioned closest to the fixture part. The purpose of this portion is to overbridge the tissue or gingiva of a patient. The abutment part tissue extending portion may, depending on the thickness of the patient's gingiva, have a height in the axial direction of 0.5 to 5 mm. A second portion is what may be called the abutment part crown engaging portion. This is the portion of the abutment part that, when a coronal component is attached to the implant, may be in contact with and support the coronal component. The coronal component may be a crown, but it may for example also be a waxing sleeve, a burn-out cylinder, a part of a dental bridge, an impression pick-up or any other coronal component. The height of this portion may vary between 1 to 5 mm depending on the configuration of the dental implant. If the abutment structure is configured so that the abutment screw is intended to carry most of the forces acting upon the abutment structure during use, the abutment part crown engaging portion may be between 1 to 2 mm in the axial direction. However, in another design the abutment part may carry a larger portion of the forces acting upon the abutment structure, and the length of the abutment part crown engaging portion may then be between 2 and 5 mm. It may also be preferred that the height of the abutment part crown engaging portion is between 2 and 2.5 mm. This height may be suitable for carrying some of the forces that may be applied to the coronal component during use, i.e. mainly the rotational forces applied on the dental implant. It may also be a suitable size in order to be able to provide rotational stops at the abutment part. The third portion of the abutment structure extending coronally of the fixture part is the coronal end portion of the abutment screw. The abutment screw extends, in use, from the fixture part, preferably in a bore through the abutment part, and has a coronal end portion extending coronally of the coronal end portion of the abutment part. This coronal end portion may also be called an abutment screw crown engaging part. The length of the abutment screw crown engaging part may also vary depending on the configuration of the dental implant, e.g. depending on where in a patient's jawbone the dental implant is intended to be inserted. The length of the abutment screw crown engaging portion may therefore vary between 1 to 7 mm. The length of the abutment screw crown engaging portion may also vary depending on the length of the abutment part crown engaging portion. It may therefore be preferred that the length of the abutment screw crown engaging portion varies between 2 to 7 mm in the configuration where the length of the abutment part crown engaging portion varies between 1 to 2 mm. Furthermore, it may be preferred that the length of the abutment screw crown engaging portion varies between 1 to 6 mm in the configuration where the abutment part crown engaging portion varies between 2 to 5 mm. In the configuration where the abutment part crown engaging portion is approximately 2 to 2.5 mm, the length of abutment screw crown engaging portion may vary between 1 and 6 mm.

It may also be desirable that the total length of the portion of the abutment part and the portion of the abutment screw that during use may be in contact with the coronal component, i.e. the abutment part crown engaging portion and the abutment screw crown engaging portion, is between 3 and 8 mm. Put in other words, the total height the abutment structure may extend coronally of a patient's gingiva when an implant has been implanted is 3 to 8 mm. This may be suitable in order to support a coronal component.

Preferably, said coronal end portion of said abutment screw is arranged to, in said assembled state of said dental implant, be extending at least 1 mm coronally of said coronal end portion of said abutment part.

1 mm may be a desired minimum height in order for the coronal end portion of said abutment screw to be able to support the coronal component. The abutment screw may further be adapted so that it in an assembled state becomes positioned so that the coronal end portion of the abutment screw extends up to 7 mm coronally of the coronal end of the abutment part.

The length of the portion of said abutment part that in an assembled state of said dental implant is positioned coronally of the fixture part is preferably at least 1.5 mm. That is, the length of the abutment part tissue extending portion is at least 0.5 mm and the length of the abutment part crown engaging portion is at least 1 mm. It may however also be more preferred that the abutment part crown engaging portion is at least 2 mm, in order to carry the forces imposed on the dental implant and in order to facilitate the arranging of rotational stops at the abutment part. The length of the portion of said abutment part that in an assembled state of a dental implant is positioned coronally of the fixture part may then preferably be at least 2.5 mm. The length of said abutment screw depends partly on the length of the portion of said abutment screw that is to be positioned in said fixture part when said dental implant is assembled. Preferably, the length of the portion of the abutment screw that in the assembled state of said dental implant is positioned coronally of said fixture part is between 3.5 and 13 mm. Preferably, the abutment screw does not extend more than 7 mm, and not less than 1 mm, coronally of the coronal end portion of the abutment part. When the abutment part crown engaging portion has a length of 2 to 2.5 mm it may be preferred that the abutment screw does not extend more than 6 mm and not less than 1 mm coronally of the coronal end portion of the abutment part.

The portion of the abutment part that in an assembled state of said dental implant is positioned coronally of said fixture part is preferably at least 1.5 mm, i.e. 0.5 mm is the so called abutment part tissue extending portion and 1 mm is the so called abutment part crown engaging portion. The length of the portion of said abutment screw that in an assembled state of said dental implant is positioned coronally of said fixture part is preferably 13 mm or less. In the maximum length case, 5 mm of the abutment screw extend through the tissue extending portion of the abutment part and 8 mm is extending coronally of the tissue extending portion of the abutment part. It may however be even more preferred that the portion of the abutment part that in an assembled state of said dental implant is positioned coronally of said fixture part is at least 3 mm, e.g. 1 mm is the abutment part tissue extending portion and at least 2 mm is the abutment part crown engaging portion.

When the dental implant is assembled, the abutment screw may be extending with a portion of its length coronally of the coronal end of the abutment part. Another portion of the abutment screw may extend in a bore provided at the abutment part and a third portion of the abutment screw may be engaged with the fixture part. A portion of the abutment part may in the assembled state be positioned in the fixture. Hence, a portion of the abutment screw that is positioned in a bore in the abutment part is also positioned in the fixture.

Preferably, the diameter of said bore extending in the axial direction of said abutment part is 1.5 to 5 mm. It may be even more preferred that the diameter of said bore extending in the axial direction of said abutment part is 2 to 4 mm.

It may for certain dental implants be desired, e.g. for aesthetic reasons, to have a rather small diameter. It may then be beneficial if the diameter of the bore extending in the abutment part may be held within the above-mentioned ranges. The diameter of the abutment screw may be made with a diameter corresponding to that of the bore in the abutment part, i.e. within 1.5 to 5 mm and more preferably within 2 to 4 mm.

The diameter of the coronal end portion of the abutment screw may be within 1.5 to 5 mm.

The diameter of the coronal end portion of the abutment part may be within 2 to 5 mm.

The wall thickness of the abutment part at its coronal end may be within 0.2 to 1.5 mm.

In order to obtain the objects of the present invention, i.e. dental implants with a design that is rather elongate and that at the same time may withstand the forces it is subject to, the above-mentioned ratios may be beneficial.

A dental implant as described above is preferably used for supporting a coronal component in a patient's oral cavity.

According to another aspect of the present invention an abutment structure for use in a dental implant is provided, said abutment structure being adapted to support a cement-retained coronal component, wherein said abutment structure is adapted to be supported by a fixture part of said implant, said abutment structure comprises at least an abutment part and an abutment screw, wherein said abutment part is adapted to be fixed to said fixture part by said abutment screw, and wherein said abutment part has an axial extension such that when said abutment part is fixed to said fixture part by said abutment screw, a coronal end portion of said abutment screw will be positioned coronally of a coronal end portion of said abutment part.

According to another aspect of the present invention an abutment structure for use in a dental implant is provided, said abutment structure being adapted to be supported by a fixture part of said implant, said abutment structure comprises at least an abutment part and an abutment screw, wherein said abutment part is adapted to be fixed to said fixture part by said abutment screw, wherein said abutment screw comprises a generally cylindrical coronal portion, and wherein said abutment part has an axial extension such that when said abutment part is fixed to said fixture part by said abutment screw, a coronal end portion of said abutment screw will be positioned coronally of a coronal end portion of said abutment part.

According to another aspect of the present invention an abutment structure for use in a dental implant is provided, said abutment structure being adapted to be supported by a fixture part of said implant, said abutment structure comprises at least an abutment part and an abutment screw, wherein said abutment part is adapted to be fixed to said fixture part by said abutment screw, wherein said abutment screw comprises drive means arranged at a coronal end surface of said abutment screw, wherein said coronal end surface of said abutment screw is substantially perpendicular to an axial direction of said abutment screw, and wherein said abutment part has an axial extension such that when said abutment part is fixed to said fixture part by said abutment screw, a coronal end portion of said abutment screw will be positioned coronally of a coronal end portion of said abutment part.

A general idea of the invention is thus to provide an abutment structure which is adapted such that, when the abutment structure is assembled to a fixture part of a dental implant, a portion of the abutment screw extends coronally of the coronal end portion of the abutment part. A coronal component such as a dental crown, a part of a dental bridge, a burn-out cylinder, a healing cap, a waxing sleeve or an impression pick-up will therefore, when mounted to the abutment structure, become at least partially supported by the coronal portion of the abutment screw. It may be preferred that the coronal component also is in contact with and at least partly supported by the abutment part as well. For example, the abutment screw may support the coronal component in such a manner that it carries the force components that may act upon the coronal component in a direction perpendicular to the longitudinal axis of the dental implant. The abutment part may then support the coronal component in such a manner that it carries the rotational forces the coronal component may be subject to.

An abutment screw may be made as a solid piece. As a consequence of this, the above-mentioned problems with small wall thickness of the structure supporting the coronal component may be at least partly reduced. The strength of the abutment screw may therefore be satisfactorily high even when the diameter of the abutment screw, and hence the abutment structure, is rather small in comparison to its height. Hence, an abutment structure that is capable of handling the forces it may be subject to, both during implantation and during use, is achieved.

It may be suitable if said abutment screw comprises drive means arranged at a coronal end surface of said abutment screw, and said coronal end surface is substantially perpendicular to the axial direction of said abutment screw.

Drive means arranged at the coronal end surface of said abutment screw, i.e. the surface screw that is situated at the coronal end of said abutment screw, may be beneficial for enabling tightening and releasing of the abutment screw to and from a fixture part. The surface that the drive means are arranged at may be perpendicular in relation to the axial direction of the abutment screw. It may further be suitable that an apical portion of the abutment screw is provided with threads, in order to threadingly engage a corresponding portion of the fixture part when the abutment structure is assembled to a fixture.

Preferably, said abutment structure is intended to support a cementretained coronal component.

A coronal component may be cement-retained to the abutment structure. However, it may also be possible to provide the abutment screw and/or the abutment part with threads. By that, a coronal component may be screw-retained to the abutment structure.

Preferably, said abutment screw comprises a substantially cylindrical coronal portion.

The coronal portion of the abutment screw may also be provided with an external hexagonal profile or any other profile that may be suitable. The inner surface of the coronal component, i.e. the surface of the coronal component that during use is arranged to be in contact with the abutment structure, may preferably comprise a corresponding design.

Preferably, said drive means of said abutment screw, by which said abutment part is adapted to be fixed to said fixture part, comprises at least one notch.

A notch may be a beneficial arrangement for providing the drive means. The drive means may also comprise two notches, which may be arranged perpendicularly to and intersecting each other. Two notches may simplify the process of tightening and removing the abutment screw to and from engagement with a fixture part of a dental implant.

Preferably said coronal end portion of said abutment screw, which in an assembled state extends coronally of said abutment part, is arranged for supporting a coronal component.

This provides for the possibility to design the abutment structure with the desired shape, e.g. a design where the diameter of the abutment structure is rather small in relation to its height, and at the same time being able to withstand the forces it may be subject to.

Preferably, at least a portion of said abutment part has a conical shape tapered at least in a coronal direction of said abutment part.

It may also be preferred that at least a portion of the abutment screw has a conical shape tapered at least in a coronal direction of said abutment screw.

A tapering or angulated shape of the abutment part and/or the abutment screw assists in the positioning of a dental implant in a patient's jawbone. The shape of the jawbone where the dental implant is to be positioned may vary between different patients. Therefore, the borehole in the jawbone, in which the fixture part is to be positioned, sometimes has to be made in an inclined direction. When positioning several dental implants beside each other, a conflict may then arise when attempting to assemble the coronal component to the dental implant. This conflict may also arise with existing teeth surrounding the dental implant when only one dental implant is to be implanted. With a tapering or angulated shape of the abutment part and/or the abutment screw this conflict may be at least partly reduced. Hence, the tapered shape of either or both of the abutment part and the abutment screw increases the tolerance for drilling the holes in the patient's jawbone. It may be preferred that the abutment screw tapers at least in the portion that in an assembled state of said dental implant is adapted to extend coronally of the abutment part.

Preferably, said abutment part is provided with an internal bore extending in the axial direction of said abutment part, wherein said bore is provided with a tapering portion, which portion tapers in the apical direction of said abutment part.

Preferably, said abutment part comprises a bore, extending substantially in the axial direction of said abutment part, wherein said bore is adapted for receiving said abutment screw.

A bore extending through the abutment part for receiving the abutment screw is a beneficial manner in how to arrange for the abutment part to be fixed to a fixture of a dental implant by means of said abutment screw.

An internal bore in said abutment part is beneficial for the insertion of the abutment screw through the abutment part. It is further advantageous if said abutment part is provided with a tapered portion, and the abutment screw is provided with a corresponding portion that is adapted to abut the tapered portion of the abutment part. This tapered portion, or shoulder, may then prevent axial movement of the abutment part when the abutment structure is assembled and in use, i.e. when the abutment screw extends through the bore and is arranged in e.g. threaded engagement with a fixture part.

It may be preferred that said abutment part and/or said abutment screw is provided with a snap fitting arranged for engagement with a coronal component.

A snap fitting provided at the abutment part or the abutment screw may be beneficial in terms of mounting a coronal component to the abutment structure. The snap fitting may for example comprise a groove at the abutment part. The coronal component may then be provided with a corresponding portion that upon assembling of the coronal component to the abutment structure snaps into engagement with the groove.

It may be preferred that at least a part of said abutment part, which is intended for supporting a coronal component, is provided with means for increasing the retention capability of said abutment part.

An increased retention, or frictional, capability may be advantageous in order to prevent the coronal component from being unintentionally separated from the abutment structure and the dental implant. This increased retention capability may be provided by providing the abutment part with e.g. a blasted, etched, knurled or grooved surface.

Preferably, said abutment part is provided with one or more rotational stops for preventing an attached coronal component from rotation.

Preferably, at least a portion of an outer circumference of said abutment part, which is intended for supporting a coronal component, has a non-circular outline.

Once a coronal component is attached to the abutment structure in a desired orientation, it is advantageous to restrain the coronal component from rotation. This may be achieved by providing the abutment part with one or more rotational stops. A rotational stop may be provided by arranging one or more recesses or cut-outs at the coronal portion of the abutment part, i.e. at a crown engaging portion of the abutment part. One or several protrusions provided at an inner surface of a coronal component may then be fitted into a corresponding recess in order to prevent or limit the rotational possibilities of the coronal component in relation to the dental implant. Furthermore, by providing at least a portion of the abutment part with a non-circular outline, the rotational possibilities of an attached coronal component may be even further restrained. This non-circular outline may for example be oval, squared, rectangular or triangular. The portion of the coronal component that may be in contact with the abutment part when the coronal component is mounted on the abutment structure may then have a corresponding non-circular inner surface.

Preferably, said coronal end portion of said abutment screw, that in an assembled state of a dental implant is extending coronally of a coronal end portion of said abutment part, has a length of 1-7 mm in the axial direction.

Preferably, the portion of said abutment part that during use may be in contact with a coronal component attached to said dental implant has a length of 1-5 mm in the axial direction.

Preferably, the portion of said abutment part that during use may be in contact with a coronal component attached to said dental implant has a length of 2-2.5 mm in the axial direction.

Preferably, the total length of the portion of the abutment part and the portion of the abutment screw that during use may be in contact with and support a coronal component is 3-8 mm in the axial direction.

The portions of an abutment structure of a dental implant, which in an assembled state is positioned coronally of a fixture part of a dental implant, may be considered as three portions. A first portion is the abutment part tissue extending portion. That is the portion of the abutment part that during use is positioned closest to the fixture part. The purpose of this portion is to overbridge the tissue or gingiva of a patient. The abutment part tissue extending portion may, depending on the thickness of the patient's gingiva, have a height in the axial direction of 0.5 to 5 mm. A second portion is what may be called the abutment part crown engaging portion. This is the portion of the abutment part that, when a coronal component is attached to the abutment structure, may be in contact with and support the coronal component. The coronal component may be a crown, but it may for example also be a waxing sleeve, a burn-out cylinder, a part of a dental bridge, an impression pick-up or any other coronal component. The height of this portion may vary between 1 to 5 mm depending on the configuration of the dental implant. If the abutment structure is configured so that the abutment screw carries most of the forces acting upon the abutment structure during use, the abutment part crown engaging portion may be between 1 to 2 mm in the axial direction. However, in another design the abutment part may carry a larger portion of the forces acting upon the abutment structure, and the length of the abutment part crown engaging portion may then be between 2 and 5 mm. It may also be preferred that the axial length of the abutment part crown engaging portion is between 2 and 2.5 mm. This length may be suitable for carrying some of the forces that may be applied to the dental implant during use, i.e. mainly the rotational forces applied on the dental implant. It may also be a suitable size in order to be able to provide rotational stops at the abutment part. The third portion of the abutment structure extending coronally of the fixture part is the coronal end portion of the abutment screw. The abutment screw extends, in use, from the fixture part, preferably in a bore through the abutment part, and has a coronal end portion extending coronally of the coronal end portion of the abutment part. This coronal end portion may also be called an abutment screw crown engaging part. The length of the abutment screw crown engaging part may also vary depending on the configuration of the dental implant, e.g. depending on where in a patient's jawbone the dental implant is intended to be inserted. The length of the abutment screw crown engaging portion may therefore vary between 1 to 7 mm. The length of the abutment screw crown engaging portion may also vary depending on the length of the abutment part crown engaging portion. It may therefore be preferred that the length of the abutment screw crown engaging portion varies between 2 to 7 mm in the configuration where the length of the abutment part crown engaging portion varies between 1 to 2 mm. Furthermore, it may be preferred that the length of the abutment screw crown engaging portion varies between 1 to 6 mm in the configuration where the abutment part crown engaging portion varies between 2 to 5 mm. In the configuration where the abutment part crown engaging portion is between 2 to 2.5 mm, the length of the abutment screw crown engaging portion may vary between 1 and 6 mm.

It may also be desirable that the total length of the portion of the abutment structure that during use may be in contact with the coronal component, i.e. the abutment part crown engaging portion and the abutment screw crown engaging portion, is between 3 and 8 mm. Put in other words, the total height the abutment structure may extend coronally of a patient's gingiva when an implant has been implanted is 3 to 8 mm. This may be suitable in order to support a coronal component.

Preferably, said coronal end portion of said abutment screw is arranged to, in an assembled state, be extending at least 1 mm coronally of said coronal end portion of said abutment part.

1 mm may be a desired minimum height in order for the coronal end portion of said abutment screw to be able to support the coronal component in the intended manner. The abutment screw may further be arranged so that the coronal end portion of the abutment screw extends up to 7 mm coronally of the coronal end of the abutment part in an assembled state of said abutment structure.

The length of the portion of said abutment part that in an assembled state of a dental implant is positioned coronally of the fixture part is preferably at least 1.5 mm. That is, the length of the abutment part tissue extending portion is at least 0.5 mm and the length of the abutment part crown engaging portion is at least 1 mm. It may however also be more preferred that the abutment part crown engaging portion is at least 2 mm, in order to carry the forces imposed on the dental implant and in order to facilitate the arranging of rotational stops at the abutment part. The length of the portion of said abutment part that in an assembled state of a dental implant is positioned coronally of the fixture part may then preferably be at least 2.5 mm. The length of said abutment screw depends partly on the length of the portion of said abutment screw that is to be positioned in a fixture part when the abutment structure is assembled to a dental implant. Preferably, the length of the portion of the abutment screw that in the assembled state of said dental implant is positioned coronally of said fixture part is between 3.5 and 13 mm. Preferably, the abutment screw does not extend more than 7 mm, and not less than 1 mm, coronally of the coronal end portion of the abutment part. When the abutment part crown engaging portion has a length of 2 and 2.5 mm it may be preferred that the abutment screw does not extend more than 6 mm and not less than 1 mm coronally of the coronal end portion of the abutment part.

The portion of the abutment part that in an assembled state of a dental implant is positioned coronally of a fixture part is preferably at least 1.5 mm, i.e. the so called abutment tissue extending portion is at least 0.5 mm and the so called abutment part crown engaging portion is at least 1 mm. The length of the portion of said abutment screw that in an assembled state of a dental implant is positioned coronally of a fixture part is preferably 13 mm or less. In the maximum length case, 5 mm of the abutment screw extends through the tissue extending portion of the abutment part and 8 mm is extending coronally of the tissue extending portion of the abutment part. By that, the abutment screw may extend 7 mm coronally of the coronal end of the abutment part. It may however be even more preferred that the portion of the abutment part that in an assembled state of said dental implant is positioned coronally of said fixture part is at least 3 mm, e.g. at least 1 mm is the abutment part tissue extending portion and at least 2 mm is the abutment part crown engaging portion.

When a dental implant is assembled, the abutment screw may be extending with a portion of its length coronally of the coronal end of the abutment part. Another portion of the abutment screw may extend in a bore provided at the abutment part and a third portion of the abutment screw may be engaged with a fixture part, e.g. by threaded engagement. A portion of the abutment part may in the assembled state be positioned in the fixture part as well. Hence, a portion of the abutment screw that is positioned in a bore in the abutment part is also positioned in the fixture part.

It may further be beneficial that at least 1 mm of the abutment screw extends coronally of the abutment part when the abutment structure is assembled.

Preferably, the diameter of said bore extending in the axial direction of said abutment part is 1.5 to 5 mm.

It may be beneficial, e.g. for aesthetic reasons, to provide abutment structures in different sizes depending on where in a patient's mouth the abutment structure is to be positioned. It may therefore be beneficial that the diameter of the bore extending in the axial direction of the abutment part may vary between 1.5 to 5 mm. More specific, it may be beneficial that the diameter of said bore extending in the axial direction of said abutment part is 2 to 4 mm. The diameter of the abutment screw may consequently be provided with different diameters to fit the bore extending in the axial direction of the abutment part. Likewise, a bore provided in a fixture part that is adapted to receive the apical portion of the abutment screw may be provided in different sizes.

The diameter of the coronal end portion of the abutment screw may be within 1.5 to 5 mm.

The diameter of the coronal end portion of the abutment part may be within 2 to 5 mm.

The diameter of a bore extending in the axial direction of an abutment part is preferably corresponding to the diameter of an abutment screw that is to be extending through the bore. The diameter of the bore may preferably be within 1.5 to 5 mm. The wall thickness of the coronal end portion of the abutment part may preferably be within 0.2 to 1.5 mm. The above-mentioned ratios may be beneficial in order to provide an abutment structure with a desired shape and that may withstand the forces that may act upon it during use.

An abutment structure as described above may be beneficial to use for supporting a coronal component in a patient's oral cavity.

According to another aspect the present invention provides a method for implantation of a dental implant, said method comprising the steps of:

inserting a fixture part at least partially into bone, such that said fixture part forms an apical bone contact part of said dental implant;

arranging an abutment part in relation to said fixture part in such a manner that said abutment part is supported by said fixture part and extends coronally of said fixture part;

fixating said abutment part to said fixture part by an abutment screw, in such a manner that a coronal end portion of said abutment screw is positioned coronally of a coronal end portion of said abutment part;

arranging a coronal component in a patient's oral cavity, wherein said coronal component is supported by said abutment part and said coronally extending portion of said abutment screw; and retaining said coronal component to said dental implant by cement.

According to another aspect the present invention provides a method for implantation of a dental implant, said method comprising the steps of:

inserting a fixture part at least partially into bone, such that said fixture part forms an apical bone contact part of said dental implant;

arranging an abutment part in relation to said fixture part in such a manner that said abutment part is supported by said fixture part and extends coronally of said fixture part; and fixating said abutment part to said fixture part by an abutment screw comprising a generally cylindrical coronal portion, in such a manner that a coronal end portion of said abutment screw is positioned coronally of a coronal end portion of said abutment part.

According to another aspect the present invention provides a method for implantation of a dental implant, said method comprising the steps of:

inserting a fixture part at least partially into bone, such that said fixture part forms an apical bone contact part of said dental implant;

arranging an abutment part in relation to said fixture part in such a manner that said abutment part is supported by said fixture part and extends coronally of said fixture part; and fixating said abutment part to said fixture part by tightening an abutment screw, in such a manner that a coronal end portion of said abutment screw is positioned coronally of a coronal end portion of said abutment part, wherein said abutment screw has drive means arranged at a coronal end surface of said abutment screw, and wherein said coronal end surface is substantially perpendicular to an axial direction of said abutment screw.

Preferably, said method further comprises the steps of:

arranging a coronal component in a patient's oral cavity, wherein said coronal component is supported by said abutment part and said coronally extending portion of said abutment screw; and fixating said coronal component to said dental implant by cement.

A general idea of the invention is thus to implant a dental implant in such a manner that a portion of the abutment screw extends coronally of the coronal end portion of the abutment part. A coronal component such as a dental crown, a part of a dental bridge, a burn-out cylinder, a healing cap, a waxing sleeve or an impression pick-up may therefore, when mounted to the abutment structure, become at least partially supported by the coronal portion of the abutment screw. It may be preferred that the coronal component also is in contact with and at least partly supported by the abutment part as well. For example, the abutment screw may support the coronal component in such a manner that it carries the force components that may act upon the coronal component in a direction perpendicular to the longitudinal axis of the dental implant. The abutment part may then support the coronal component in such a manner that it carries the rotational forces the coronal component may be subject to. It may be preferred that the length of the abutment part that is in contact with and supports the coronal component has a length in the axial direction of approximately 2 to 2.5 mm. It may also be preferred that the abutment part is provided with one or more rotational stops in order to prevent an attached coronal component from rotation.

An abutment screw may be made as a solid piece. As a consequence of this, the above-mentioned problems with thin wall thickness of the part supporting the coronal component may be at least partly reduced. The strength of the abutment screw may therefore be satisfactorily high even when the diameter of the abutment screw, and hence the abutment structure, is rather small in comparison to its height.

The coronal component may thereafter be cement-retained to the abutment structure, i.e. the abutment part and the abutment screw. However, it may also be for example screw-retained.

BRIEF DESCRIPTION OF THE DRAWINGS

By way of example, embodiments of the present invention will now be described with reference to the accompanying figures of drawings, in which:

FIG. 1 is a cross-sectional view of a dental implant in an assembled state, in accordance with the present invention;

FIG. 2a is a perspective view of an abutment structure in accordance with the present invention;

FIG. 2b is a top view of the abutment structure shown in FIG. 2a.

DETAILED DESCRIPTION OF PREFERRED EMBODIMENTS OF THE INVENTION

The inventive concept relates to dental implants, abutment structures and methods for implantation of a dental implant.

An embodiment of the inventive concept will now be described in relation to FIGS. 1 to 2b.

The implant 1 is a dental implant for implantation into a maxilla or mandible of a patient and it is adapted to support a coronal component such as a crown, a part of a dental bridge, a burn-out cylinder, a healing cap, a waxing sleeve or an impression pick-up.

The dental implant 1 comprises a fixture part 5 having a generally cylindrical shape. The length of the fixture part is preferably between 6-19 mm and the maximum width around 3-6 mm. The fixture part 5 is adapted for insertion into a bore hole drilled in the bone tissue of a maxilla or a mandible. The fixture 5 is made from commercially pure titanium, a titanium alloy, another biocompatible metal or metal alloy or a ceramic to promote osseointegration of the implant with the bone tissue of the boundary walls of the borehole.

The fixture has a cancellous portion presenting a cylindrical outer surface, and a cortical portion that, when installed in a borehole in bone tissue, generally engage the cortical bone tissue layer.

The fixture 5 is provided with a socket having an open end in the uppermost portion for receiving an abutment structure 2, which will bridge the gingiva 15 overlying the borehole and support/present the coronal component.

The abutment structure 2 comprises at least two parts, an abutment part 3 and an abutment screw 4 that is adapted to secure the abutment part 3 to the fixture 5. The abutment structure 2 may be provided in several different lengths. The desired length of the abutment structure 2 varies depending on where in the patient's mouth it is intended to be inserted and also on the thickness of the gingiva 15 of the respective patient at the respective position in the mouth. It may for example vary between 3.5 mm and 13 mm, counted from the coronal portion of the fixture part when the implant is in assembled state. The total length of the abutment screw 4, in the axial direction, may vary between 6 mm and 21 mm. The total length of the abutment part 3, also in the axial direction, may vary between 1.5 mm and 15 mm. As may also be seen in FIG. 1, a portion of the abutment screw that is positioned in a bore in the abutment part is also positioned in the fixture. The length of the portion of the abutment screw that in an assembled state is positioned coronally of the apical end of the abutment part is preferably between 3.5 and 18 mm.

The abutment part 3 is in this embodiment provided with a hexagonal lower portion 6, which is to be inserted into the fixture part 5 when implanting the dental implant. The abutment part 3 may be inserted into the fixture part 5 immediately after implanting the fixture part 5 into the patient's bone, but it may also be inserted at a later time. The fixture part 5 is provided with a corresponding portion for receiving the abutment part 3. The hexagonal profile 6 prevents rotation of the abutment part 3 in relation to the fixture 5. The abutment part 3 is, also in the assembled state of the dental implant 1, secured to the fixture by the abutment screw 4, which prevents the abutment part 3 from axial displacement in relation to the fixture part 5, i.e. prevents the abutment part 3 from being removed from the fixture. As may be seen in FIG. 1, the hole extending through the abutment part 3, for receiving the abutment screw 4, is not uniformly shaped. It has a sloping or angulated surface 7 which functions as a seat for the abutment screw 4. The abutment screw 4 is, as may also be seen in FIG. 1, provided with a correspondingly shaped angulated portion 8. As may also be seen in FIG. 2a, the abutment screw 4 is provided with a threaded portion at its apical portion. This threaded portion is arranged for threadingly engage a corresponding portion of the fixture part 5 of the dental implant.

The abutment screw 4 is at its coronal end provided with two notches 13, which are arranged at right angles in relation to each other and which intersect each other. These notches 13 may receive a corresponding tool and serves then as drive means for tightening the abutment screw 4 to the fixture part 5, and also for releasing the abutment screw 4 from the fixture part 5.

The portion 10 of the abutment part 3 that in an assembled state of said dental implant is positioned coronally of the fixture, i.e. extends outside the coronal end of the fixture, is preferably between 1.5 and 10 mm, and even more preferred, between 3 and 8 mm. The portion 11 of the abutment screw 4 that in an assembled state of said dental implant is positioned coronally of the fixture, i.e. likewise extends outside the coronal end of the fixture, is preferably between 3.5 and 13 mm. The length of the portion 21 of the abutment part 3, i.e. the length of the portion of the abutment part that extends coronally of the surface of the patient's gingiva 15 in an assembled state, may be between 1 and 5 mm. However, in this embodiment it is preferred that it is between 2 and 2.5 mm. The portion 23 of the abutment part, i.e. the portion that in an assembled state of the dental implant overbridges the patient's gingiva may have a length of 0.5 to 5 mm. The total height 22 from the surface of the patient's gingiva 15 to the coronal end of the abutment structure 2, i.e. the coronal end surface 16 of the abutment screw 4, may be between 3 and 8 mm.

As may be seen in FIG. 1, showing the dental implant in its assembled state, the coronal end portion 9 of the abutment screw 4 is positioned coronally of the coronal end portion 18 of the abutment part 3. This coronal end portion 9 of the abutment screw 4 may be between 1 to 7 mm. The portion 23 of the abutment part may be considered as an abutment part tissue extending portion. The portion 21 of the abutment part may be considered an abutment part crown engaging portion. The portion 9 of the abutment screw may be considered an abutment screw crown engaging portion. Hence, it is with this configuration possible to utilize both the coronal portion of the abutment screw 4, i.e. the abutment screw crown engaging portion 9, and the coronal portion of the abutment part 3, i.e. the abutment part crown engaging portion 21, to support a coronal component. A height of 2 to 2.5 mm of the abutment part crown engaging portion is in this embodiment suitable in order to carry the forces imposed on the dental implant, and also suitable for facilitating the arrangement of one or more rotational stops at the abutment part crown engaging portion.

As may be seen in FIGS. 1 to 2b, the portion of the abutment part 3 that is intended to be positioned coronally of the gingiva 15 when implanted into a patient's mouth is slightly angulated or tapering. This angulation may for example be 6°. As may be seen in FIGS. 1 to 2, the abutment screw 4 also has a conical shape tapered in the coronal direction. The abutment screw 4 tapers at least in a portion of the portion extending outside the abutment part 3. This angulation may for example be 4 to 8°. The purpose of these angulations are to be able to position several dental implants beside each other, i.e. when replacing several teeth, without the coronal components that is to be secured to each dental implants coming in conflict with each other or with surrounding teeth, for example during mounting or dismounting of the coronal components.

Below the slightly angulated portion of the abutment part 3, the abutment part 3 is provided with a notch 12, which serves as a snap on feature. The coronal component is provided with a portion that corresponds to the notch and when mounting the coronal component to the dental implant, the coronal component is thereby held by the dental implant. The notch 12, i.e. the snap on feature, may also be arranged at the coronal portion 9 of the abutment screw, i.e. the portion of the abutment screw that in an assembled state of the dental implant extends coronally of the abutment part.

The portion of the abutment part 3 that is to be in contact with the coronal component may be sandblasted for increased retention capabilities, i.e. the friction of the portion of the abutment part 3 may be increased. Other means to increase the retention capability, or the friction, of the abutment part 3 may be to knurl, etch or groove the portion of the abutment part 3 that is to be in contact with the coronal component. As may also be seen in FIG. 2a, the abutment part is provided with a defined rotational stop 20 for preventing an attached coronal component from rotation. The rotational stop is in this embodiment provided by a recess in the coronal portion of the abutment part. A projection arranged at the inner surface of a coronal component may upon assembly be fitted into the recess and thereby the coronal component is prevented, or at least obstructed, from rotation in relation to the dental implant.

As may be see in FIG. 2b, the circumference of the abutment part 3 is in this embodiment oval. The reason for this is to restrain or prevent the coronal component from being able to rotate in relation to the abutment part 3 and thus the fixture 1. It is however not necessary that the abutment part 3 has an oval outline. For example, a triangular, squared or rectangular outline does also assist in preventing the coronal component from rotation in relation to the abutment part 3.

The diameter of the abutment screw 4, and the size of the implant is dependent on where in the patient's jawbone it is to be implanted. Therefore, the diameter of the abutment screw 4, and consequently the hole through the abutment part 3, may vary between approximately 1.5 to 5 mm.

When implanting a dental implant according to the inventive concept, a fixture is first inserted into a borehole in the patient's jawbone. Thereafter the lower hexagonal portion of the abutment part 3 is inserted into the corresponding opening of the fixture in such a manner that it becomes rotationally locked in relation to the fixture part 5. The abutment screw 4 is thereafter inserted into the bore 17 extending through the abutment part 3. An operator thereafter, by means of the notches 13, threadingly secures the lower portion of the abutment screw 4 with the corresponding portion of the fixture part 5. Thereafter a coronal component may be mounted and secured to the abutment structure 2.

It will be appreciated that the invention has been illustrated with reference to exemplary embodiments and that the invention can be varied in many different ways within the scope of the appended claims.

The invention claimed is:

1. A dental implant for supporting a cement-retained coronal component, said implant comprising:
   a fixture part forming an apical bone contact part of said implant;
   an abutment part forming a coronal component support part of said implant, and
   an abutment screw, wherein said abutment part is arranged to, in an assembled state of said dental implant, be fixed to said fixture part by said abutment screw, and wherein a coronal end portion of said abutment screw is arranged to, in said assembled state, extend beyond a coronal end of a coronal end portion of said abutment part,
   wherein at least a portion of said abutment part has a conical shape tapered at least in a coronal direction of said dental implant,
   wherein at least a portion of the coronal end portion of said abutment screw is conical in shape and tapered in the coronal direction of the dental implant,
   wherein a coronal portion of the abutment part is provided with one or more rotational stops configured to prevent an attached coronal component from rotation.

2. A dental implant according to claim 1, wherein said abutment screw comprises at least one drive device arranged at a coronal end surface of said abutment screw, and wherein said coronal end surface is substantially perpendicular to an axial direction of said abutment screw.

3. A dental implant according to claim 1, wherein said abutment screw comprises a substantially cylindrical coronal portion.

4. A dental implant according to claim 1, wherein said coronal end portion of said abutment screw forms a coronal end portion of said dental implant.

5. A dental implant according to claim 1, wherein said coronal end portion of said abutment screw extending coronally of said abutment part is arranged for supporting said coronal component.

6. A dental implant according to claim 1, wherein said abutment part is provided with an internal bore extending in the axial direction of said abutment part, wherein said bore is provided with a tapering portion, which portion tapers in the apical direction of said abutment part.

7. A dental implant according to claim 1, wherein said abutment screw is arranged to, in said assembled state of said dental implant, extend in a bore arranged in said abutment part and said fixture part, respectively.

8. A dental implant according to any claim 1, wherein said abutment part or said abutment screw is provided with a snap fitting arranged for engagement with said coronal component.

9. A dental implant according to claim 1, wherein at least a part of said abutment part, which is intended for supporting said coronal component, is provided with means for increasing the retention capability of said abutment part (3).

10. A dental implant according to claim 1, wherein the one or more rotational stops are notches in said abutment part, the notches being configured to expose additional portions of an outer surface of the abutment screw to allow cement to adhere to the exposed additional portions of the abutment screw and an outer surface of the abutment part to prevent the coronal component from rotating.

11. A dental implant according to claim 1, wherein at least a portion of an outer circumference of said abutment part, which is intended for supporting said coronal component, has a non-circular outline.

12. A dental implant according to claim 1, wherein said coronal end portion of said abutment screw, that in said assembled state of said dental implant is extending coronally of a coronal end portion of said abutment part, has a length of 1-7 mm in the axial direction.

13. A dental implant according to claim 1, wherein the portion of said abutment part that during use may be in contact with a coronal component attached to said dental implant has a length of 1-5 mm in the axial direction.

14. A dental implant according to claim 1, wherein the portion of said abutment part that during use may be in contact with a coronal component attached to said dental implant has a length of 2-2.5 mm in the axial direction.

15. A dental implant according to claim 1, wherein the total length of the portion of the abutment part and the portion of the abutment screw that during use may be in contact with and support a coronal component is 3-8 mm in the axial direction.

16. A dental implant according to claim 1, wherein said coronal end portion of said abutment screw is arranged to, in said assembled state of said dental implant, be extending at least 1 mm coronally of said coronal end portion of said abutment part.

17. A dental implant according to claim 1, wherein the diameter of said bore extending in the axial direction of said abutment part is 1.5 to 5 mm.

18. A dental implant according to claim 1, wherein the diameter of said bore extending in the axial direction of said abutment part is 2 to 4 mm.

19. A method comprising:
using a dental implant according to claim 1 for supporting a coronal component in a patient's oral cavity.

20. A dental implant comprising:
a fixture part forming an apical bone contact part of said implant;
an abutment part forming a coronal component support part of said implant; and
an abutment screw including a generally cylindrical coronal portion, wherein said abutment part is arranged to, in an assembled state of said dental implant, be fixed to said fixture part by said abutment screw, and wherein a coronal end portion of said abutment screw is arranged to, in said assembled state, extend beyond a coronal end of a coronal end portion of said abutment part,
wherein at least a portion of said abutment part has a conical shape tapered at least in a coronal direction of said dental implant,
wherein at least a portion of the coronal end portion of said abutment screw is conical in shape and tapered in the coronal direction of the dental implant,
wherein a coronal portion of the abutment part is provided with one or more rotational stops configured to prevent an attached coronal component from rotation.

21. A dental implant according to claim 20, wherein said dental implant is adapted to support a cement-retained coronal component.

22. A dental implant according to claim 20, wherein said abutment screw comprises at least one drive device arranged at a coronal end surface of said abutment screw, and wherein said coronal end surface is substantially perpendicular to an axial direction of said abutment screw.

23. A dental implant comprising:
a fixture part forming an apical bone contact part of said implant;
an abutment part forming a coronal component support part of said implant; and
an abutment screw, wherein said abutment part is arranged to, in an assembled state of said dental implant, be fixed to said fixture part by said abutment screw, wherein said abutment screw includes at least one drive device arranged at a coronal end surface of said abutment screw, wherein said coronal end surface is substantially perpendicular to an axial direction of said abutment screw, and wherein a coronal end portion of said abutment screw is arranged to, in said assembled state, extend beyond a coronal end of a coronal end portion of said abutment part,
wherein at least a portion of said abutment part has a conical shape tapered at least in a coronal direction of said dental implant,
wherein at least a portion of the coronal end portion of said abutment screw is conical in shape and tapered in the coronal direction of the dental implant,
wherein a coronal portion of the abutment part is provided with one or more rotational stops configured to prevent an attached coronal component from rotation.

24. A dental implant according to claim 23, wherein said at least one drive device of said abutment screw comprises at least one notch.

25. A dental implant according to claim 23, wherein said dental implant is adapted to support a cement-retained coronal component.

26. A dental implant according to claim 23, wherein said abutment screw comprises a substantially cylindrical coronal portion.

27. An abutment structure for use in a dental implant adapted to support a cement-retained coronal component, wherein said abutment structure is adapted to be supported by a fixture part of said implant, said abutment structure comprising:
- at least an abutment part; and
- an abutment screw, wherein said abutment part is adapted to be fixed to said fixture part by said abutment screw, and wherein said abutment part has an axial extension such that when said abutment part is fixed to said fixture part by said abutment screw, a coronal end portion of said abutment screw will extend beyond a coronal end of a coronal end portion of said abutment part,
- wherein at least a portion of said abutment part has a conical shape tapered at least in a coronal direction of said dental implant,
- wherein at least a portion of the coronal end portion of said abutment screw is conical in shape and tapered in the coronal direction of the dental implant,
- wherein a coronal portion of the abutment part is provided with one or more rotational stops configured to prevent an attached coronal component from rotation.

28. An abutment structure according to claim 27, wherein said abutment screw includes at least one drive device arranged at a coronal end surface of said abutment screw, and wherein said coronal end surface is substantially perpendicular to the axial direction of said abutment screw.

29. An abutment structure according to claim 27, wherein said abutment screw includes a substantially cylindrical coronal portion.

30. An abutment structure according to claim 27, wherein said coronal end portion of said abutment screw, which in an assembled state extends coronally of said abutment part, is arranged for supporting a coronal component.

31. An abutment structure according to claim 27, wherein said abutment part is provided with an internal bore extending in the axial direction of said abutment part, wherein said bore is provided with a tapering portion, which portion tapers in the apical direction of said abutment part.

32. An abutment structure according to claim 27, wherein said abutment part includes a bore, extending substantially in the axial direction of said abutment part, wherein said bore is adapted for receiving said abutment screw.

33. An abutment structure according to claim 27, wherein at least one of said abutment part and said abutment screw is provided with a snap fitting arranged for engagement with a coronal component.

34. An abutment structure according to claim 27 wherein at least a part of said abutment part, which is intended for supporting a coronal component, is provided with means for increasing the retention capability of said abutment part.

35. An abutment structure according to claim 27, wherein the one or more rotational stops are notches in said abutment part, the notches being configured to expose additional portions of an outer surface of the abutment screw to allow cement to adhere to the exposed additional portions of the abutment screw and an outer surface of the abutment part to prevent the coronal component from rotating.

36. An abutment structure according to claim 27, wherein at least a portion of an outer circumference of said abutment part, intended to support a coronal component, includes a non-circular outline.

37. An abutment structure according to claim 27, wherein said coronal end portion of said abutment screw, that in an assembled state of a dental implant is extending coronally of a coronal end portion of said abutment part, has a length of 1-7 mm in the axial direction.

38. An abutment structure according to claim 27, wherein the portion of said abutment part that during use may be in contact with a coronal component attached to said dental implant has a length of 1-5 mm in the axial direction.

39. An abutment structure according to claim 27, wherein the portion of said abutment part that during use may be in contact with a coronal component attached to said dental implant has a length of 2-2.5 mm in the axial direction.

40. An abutment structure according to claim 27, wherein the total length of the portion of the abutment part and the portion of the abutment screw that during use may be in contact with and support a coronal component is 3-8 mm in the axial direction.

41. An abutment structure according to claim 27, wherein said coronal end portion of said abutment screw is arranged to, in an assembled state, be extending at least 1 mm coronally of said coronal end portion of said abutment part.

42. An abutment structure according to claim 27, wherein the diameter of said bore extending in the axial direction of said abutment part is 1.5 to 5 mm.

43. An abutment structure according to claim 27, wherein the diameter of said bore extending in the axial direction of said abutment part is 2 to 4 mm.

44. A method, comprising:
- using an abutment structure according to claim 27, for supporting a coronal component in a patient's oral cavity.

45. An abutment structure for use in a dental implant, wherein said abutment structure is adapted to be supported by a fixture part of said implant, said abutment structure comprising:
- at least an abutment part; and
- an abutment screw, wherein said abutment part is adapted to be fixed to said fixture part by said abutment screw, wherein said abutment screw includes a generally cylindrical coronal portion, and wherein said abutment part has an axial extension such that when said abutment part is fixed to said fixture part by said abutment screw, a coronal end portion of said abutment screw extending beyond a coronal end of a coronal end portion of said abutment part,
- wherein at least a portion of said abutment part has a conical shape tapered at least in a coronal direction of said dental implant,
- wherein at least a portion of the coronal end portion of said abutment screw is conical in shape and tapered in the coronal direction of the dental implant.
- wherein a coronal portion of the abutment part is provided with one or more rotational stops configured to prevent an attached coronal component from rotation.

46. An abutment structure according to claim 45, wherein said abutment structure is intended to support a cement-retained coronal component.

47. An abutment structure for use in a dental implant, wherein said abutment structure is adapted to be supported by a fixture part of said implant, said abutment structure comprising:

at least an abutment part; and an abutment screw, wherein said abutment part is adapted to be fixed to said fixture part by said abutment screw, wherein said abutment screw includes at least one drive device arranged at a coronal end surface of said abutment screw, wherein said coronal end surface of said abutment screw is substantially perpendicular to an axial direction of said abutment screw, and wherein said abutment part has an axial extension such that when said abutment part is fixed to said fixture part by said abutment screw, a coronal end portion of said abutment screw extending beyond a coronal end of a coronal end portion of said abutment part, wherein at least a portion of said abutment part has a conical shape tapered at least in a coronal direction of said dental implant, wherein at least a portion of the coronal end portion of said abutment screw is conical in shape and tapered in the coronal direction of the dental implant, wherein a coronal portion of the abutment part is provided with one or more rotational stops configured to prevent an attached coronal component from rotation.

48. An abutment structure according to claim 47, wherein said at least one drive device of said abutment screw, by which said abutment part is adapted to be fixed to said fixture part, includes at least one notch.

49. A method for implantation of a dental implant, said method comprising:

inserting a fixture part at least partially into bone, such that said fixture part forms an apical bone contact part of said dental implant;

arranging an abutment part in relation to said fixture part in such a manner that said abutment part is supported by said fixture part and extends coronally of said fixture part, wherein at least a portion of said abutment part has a conical shape tapered at least in a coronal direction of said dental implant;

fixating said abutment part to said fixture part by an abutment screw, in such a manner that a coronal end portion of said abutment screw extends beyond a coronal end of a coronal end portion of said abutment part, wherein at least a portion of the coronal end portion of said abutment screw is conical in shape and tapered in the coronal direction of the dental implant;

arranging a coronal component in a patient's oral cavity, wherein said coronal component is supported by said abutment part and said coronally extending portion of said abutment screw;

providing a coronal portion of the abutment part with one or more rotational stops, the notches exposing additional portions of an outer surface of the abutment screw;

retaining said coronal component to said dental implant by cement; and preventing rotation of said coronal component by allowing the cement to adhere to the exposed additional portions of the abutment screw and an outer surface of the abutment part.

50. A method for implantation of a dental implant, said method comprising:

inserting a fixture part at least partially into bone, such that said fixture part forms an apical bone contact part of said dental implant;

arranging an abutment part in relation to said fixture part in such a manner that said abutment part is supported by said fixture part and extends coronally of said fixture part, wherein at least a portion of said abutment part has a conical shape tapered at least in a coronal direction of said dental implant;

fixating said abutment part to said fixture part by an abutment screw including a generally cylindrical coronal portion, in such a manner that a coronal end portion of said abutment screw extends beyond a coronal end of a coronal end portion of said abutment part, wherein at least a portion of the coronal end portion of said abutment screw is conical in shape and tapered in the coronal direction of the dental implant; and providing a coronal portion of the abutment part with one or more rotational stops.

51. A method according to claim 50, further comprising:

the providing of the one or more rotational stops including cutting notches in the coronal portion of the abutment part to expose additional portions of an outer surface of the abutment screw;

arranging a coronal component in a patient's oral cavity, wherein said coronal component is supported by said abutment part and said coronally extending portion of said abutment screw;

fixating said coronal component to said dental implant by cement; and preventing rotation of said coronal component by allowing the cement to adhere to the exposed additional portions of the outer surface of the abutment screw and an outer surface of the abutment part.

52. A method for implantation of a dental implant, said method comprising:

inserting a fixture part at least partially into bone, such that said fixture part forms an apical bone contact part of said dental implant;

arranging an abutment part in relation to said fixture part in such a manner that said abutment part is supported by said fixture part and extends coronally of said fixture part, wherein at least a portion of said abutment part has a conical shape tapered at least in a coronal direction of said dental implant;

fixating said abutment part to said fixture part by tightening an abutment screw, in such a manner that a coronal end portion of said abutment screw extends beyond a coronal end of a coronal end portion of said abutment part, wherein at least a portion of the coronal end portion of said abutment screw is conical in shape and tapered in the coronal direction of the dental implant, wherein said abutment screw includes at least one drive device arranged at a coronal end surface of said abutment screw, and wherein said coronal end surface is substantially perpendicular to an axial direction of said abutment screw; and providing a coronal portion of the abutment part with one or more rotational stops.

53. A dental implant for supporting a cement-retained coronal component, said implant comprising:

a fixture part forming an apical bone contact part of said implant;

an abutment part forming a coronal component support part of said implant, and a solid substantially cylindrical abutment screw, wherein said abutment part is arranged to, in an assembled state of said dental implant, be fixed to said fixture part by said abutment screw, and wherein a coronal end portion of said abutment screw is arranged to, in said assembled state, extend beyond a coronal end of a coronal end portion of said abutment part, wherein a coronal portion of the abutment part is provided with one or more rotational stops configured to prevent an attached coronal component from rotation.

* * * * *